US008323299B2

(12) United States Patent (10) Patent No.: US 8,323,299 B2
Urin et al. (45) Date of Patent: Dec. 4, 2012

(54) DEVICE FOR PREPARING TISSUE FOR ANASTOMOSIS

(75) Inventors: Yuri Urin, Haifa (IL); Igor Waysbeyn, Haifa (IL); Irina Vaysbeyn, Haifa (IL)

(73) Assignee: HDH Medical Ltd., Haifa (IL)

( * ) Notice: Subject to any disclaimer, the term of this patent is extended or adjusted under 35 U.S.C. 154(b) by 527 days.

(21) Appl. No.: 11/989,963

(22) PCT Filed: Aug. 10, 2006

(86) PCT No.: PCT/IL2006/000923
§ 371 (c)(1),
(2), (4) Date: Jan. 11, 2010

(87) PCT Pub. No.: WO2007/066317
PCT Pub. Date: Jun. 14, 2007

(65) Prior Publication Data
US 2010/0160927 A1 Jun. 24, 2010

(51) Int. Cl.
*A61B 17/04* (2006.01)
*A61F 11/00* (2006.01)
(52) U.S. Cl. ........................................ 606/149; 606/108
(58) Field of Classification Search .................. 606/149, 606/108, 150, 153–155; 227/179.1, 19, 175.1; 604/264–284; 623/1.11–1.13, 1.23; 600/36; 138/97–98
See application file for complete search history.

(56) References Cited

U.S. PATENT DOCUMENTS

| 2,156,339 | A | 5/1939 | Hom |
| 2,626,090 | A | 1/1953 | Horsley |
| 3,057,355 | A * | 10/1962 | Smialowski et al. ......... 606/149 |
| 3,945,542 | A | 3/1976 | Taylor |
| 4,281,781 | A | 8/1981 | Pope |
| 6,402,764 | B1 * | 6/2002 | Hendricksen et al. ....... 606/149 |
| 6,575,985 | B2 * | 6/2003 | Knight et al. ................. 606/149 |
| 6,719,769 | B2 | 4/2004 | Donohoe et al. |
| 6,740,101 | B2 | 5/2004 | Houser et al. |
| 6,955,679 | B1 * | 10/2005 | Hendricksen et al. ....... 606/149 |
| 6,962,595 | B1 * | 11/2005 | Chamness et al. ............ 606/153 |
| 8,105,345 | B2 * | 1/2012 | Golden et al. ................ 606/153 |
| 2003/0032968 | A1 | 2/2003 | Kirsch et al. |
| 2003/0130671 | A1 | 7/2003 | Duhaylongsod et al. |
| 2003/0135227 | A1 | 7/2003 | Chapman |
| 2005/0038502 | A1 | 2/2005 | Waysbeyn et al. |

OTHER PUBLICATIONS

International Search Report for International Application No. PCT/IL06/00923 mailed Aug. 28, 2007.

* cited by examiner

*Primary Examiner* — Gary Jackson
*Assistant Examiner* — Amy Shipley
(74) *Attorney, Agent, or Firm* — Pearl Cohen Zedek Latzer, LLP

(57) ABSTRACT

A device and method for preparation of a graft and a fastener for coupling to a vessel. The device includes a tubular body with a gripping head at a distal end to grip the graft and the fastener. The graft is threaded through the fastener and an edge of the graft out of the fastener. The gripping head has at least three segments arranged around its axis. The segments can be brought closer or pushed away from each other to modify the external diameter of the head and to provide firm gripping of the fastener and the graft. The device further includes a pliant tongue which may rotate around the tubular body. Radial positioning of the tongue may be controlled and the tongue may slide axially towards or away from the head.

17 Claims, 11 Drawing Sheets

DEVICE FOR PREPARING TISSUE FOR ANASTOMOSIS

CROSS-REFERENCE TO RELATED APPLICATIONS

This application is a National Phase Application of PCT International Application No. PCT/IL2006/000923, entitled "DEVICE FOR PREPARING TISSUE FOR ANASTOMOSIS", International Filing Date Aug. 10, 2006, published on Jun. 14, 2007 as International Publication No. WO 2007/066317, which in turn claims priority from US Provisional Patent Application No. 60/705,422, filed Aug. 4, 2005, both of which are incorporated herein by reference in their entirety.

BACKGROUND OF THE INVENTION

Devices and methods for everting tubular objects inside out are known. In some examples, the material of the object is pierced by hooks that hold the material and enable everting of the material. In these examples the material and the quality of the final outcome may be damaged as a result of the several holes pierced in it. In other examples, an end of a fabric tube is clamped between grips and pulled out to evert the material. In further other examples, tissue in the human body is everted using piercing prongs in a process which may cause damage to the tissue. Some of the known devices and methods are complicated and difficult for use and are not suitable for quick, easy and clean actions as required, for example, in operating rooms. Some of the known devices and methods are not safe and unreliable. Some of the known devices and methods do not enable full everting. U.S. Pat. No. 2,156,339 relates to a mechanism for reversing material in tubular form and, more specifically, to attaching means for use in connection therewith. U.S. Pat. No. 2,626,090 relates to a device for turning or reversing elongated tubular fabric articles such as belts, or the like. U.S. Pat. No. 3,945,542 discloses a device and method for manually everting a cloth or fabric tube where all manipulations may be visually monitored. U.S. Pat. No. 4,281,781 discloses a method of everting a knitted sleeve-like portion of wearing apparel, or the like. U.S. Patent Application Publication No. 2003/0032968 discloses a device and method for securing the urethra to the bladder in surgery by means of one or more everting prongs, which risks the intactness of the urethra and bladder. Some of these devices and methods are complicated and difficult for use and are not suitable for quick, easy and clean actions as required, for example, in operating rooms. Some of these devices and methods are not safe enough because damage may be caused to the everted materials.

Devices and methods for coupling grafts to vessels are known. U.S. Patent Application Publication No. 2003/0130671 discloses a method for coupling a first vessel and a second vessel in an anastomosis. U.S. Patent Application Publication No. 2003/0135227 discloses an anastomosis device for use in coupling an end of a graft vessel to a side of a target vessel. U.S. Pat. No. 6,740,101 discloses anastomosis systems which include fittings and compression mechanisms for affecting end-end or end-side couplings of biological or synthetic bypass grafts to vessel locations. Some of these devices and methods are difficult to use and time consuming, especially for small graft diameters. Some of these devices and methods expose foreign material to the blood flow path within the vessels, which increases the risks of hemolysis and thrombosis.

The known devices and methods are, as described above, based on the simultaneous everting of all the perimeter of an expandable tube end. These devices and methods require especially high elasticity of the material. In each of these methods and devices the everting becomes more difficult and unreliable as the diameter of the tube gets smaller.

U.S. Patent Application Publication No. 2005/0038502 discloses docking heads to be mounted on a graft so as to establish a vascular device that is coupled to a blood vessel with aneurysm, and dedicated delivery devices as well as methods of coupling. The vascular device comprises a graft having docking head at the proximal portion and another docking head at its distal portion, or two docking heads if the graft is bifurcated. The docking heads comprises a hollow truncated cone having a passage adapted to correspond to the outer diameter of the graft and is provided with a plurality of outwardly pointing and inclined barbs. The vascular device is coupled to the blood vessel on both sides of the aneurysm while the docking heads act as guiding, anchoring and sealing means in a suture-less and rapid manner. The vascular device is modular and can be prepared according to the condition of the aneurysm and the dimensions of the blood vessels during operation.

SUMMARY OF THE PRESENT INVENTION

Some embodiments of the present invention may include a device and/or method to enable easy and quick preparation of a graft and a fastener such as, for example, the docking heads described in U.S. 2005/0038502, for coupling to a vessel. Preparation of a graft and a fastener by gradually everting an edge of the graft over the fastener provides minimum stretching of the elastic graft, so that no damage to the graft may be caused and no extreme requirements on the elasticity of the graft are needed. Embodiments of the present invention may not require or cause piercing of the graft and therefore avoid possible damage to the graft. The easiness and quickness of the preparation of a fastener and graft according to embodiments of the present invention are especially important when used in operating rooms. The preparation according to embodiments of the present invention remains easy, quick and safe when the diameter of the graft gets smaller.

According to an embodiment of the present invention, a device for preparation of a graft and a fastener for coupling to a vessel may include a tubular body with a gripping head at a distal end to grip a tubular elastic object and a tubular inelastic object, wherein the elastic object may be threadable through the inelastic object, wherein an edge of the elastic object may emerge out of the inelastic object and wherein the external diameter of the head may be modifiable. The head of a device according to embodiment of the present invention may include, for example, at least three segments arranged around the axis of the head, wherein the segments can be brought closer or pushed away from each other to modify the external diameter of the head. A device according to an embodiment of the present invention may further include a pliant tongue which may be rotatable around the tubular body, wherein radial position of the tongue may be controllable, wherein the tongue may be axially slidable towards the grip head or away from the grip head.

A device according to an embodiment of the present invention may further include a collet mandrel which may be insertable to the tubular body, wherein insertion of the collet mandrel into the tubular body may push the segments away from each other thus enlarging the external diameter of the head.

A device according to an embodiment of the present invention may further include a springy cam which may be rotatable around the tubular body to limit at least one of lateral movement and radial movement of the tongue. The springy cam may position the tongue in a prescribed radial position. The springy cam may further include a first shoulder to limit insertion of the inelastic object on the head. The springy cam may further include a second shoulder to indicate proper insertion of the elastic object to enable everting of the edge on the inelastic object. The springy cam may further include a regulator to control radial position of the tongue.

A device according to an embodiment of the present invention may further include a conical section, wherein the tongue may be slidable on the conical section. The conical section may include a shoulder to limit insertion of the inelastic object on the head.

According to an embodiment of the present invention, a method for preparation of a graft and a fastener for coupling to a vessel may include the step of threading a tubular elastic object through a tubular inelastic object, wherein an edge of the elastic object may emerge out of the inelastic object. A method according to an embodiment of the present invention may further include the steps of inserting the inelastic object together with the threaded elastic object on a grip head a part of the edge being pushed by, for example, the distal edge of a pliant tongue, which is in contact with the tongue, folding the part of the edge over the inelastic object, for example by further sliding the tongue over the inelastic object or sliding the edge over the tongue, and rotating the tongue around the inelastic object to gradually evert the edge over the inelastic object.

A method according to an embodiment of the present invention may further include the step of modifying the external diameter of the grip head to reach firm griping of the inelastic object and the threaded elastic object.

A method according to an embodiment of the present invention may further include the step of sliding the tongue under the edge of the elastic object.

A method according to an embodiment of the present invention may further include the step of regulating the radial position of the tongue.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

Figure 1:
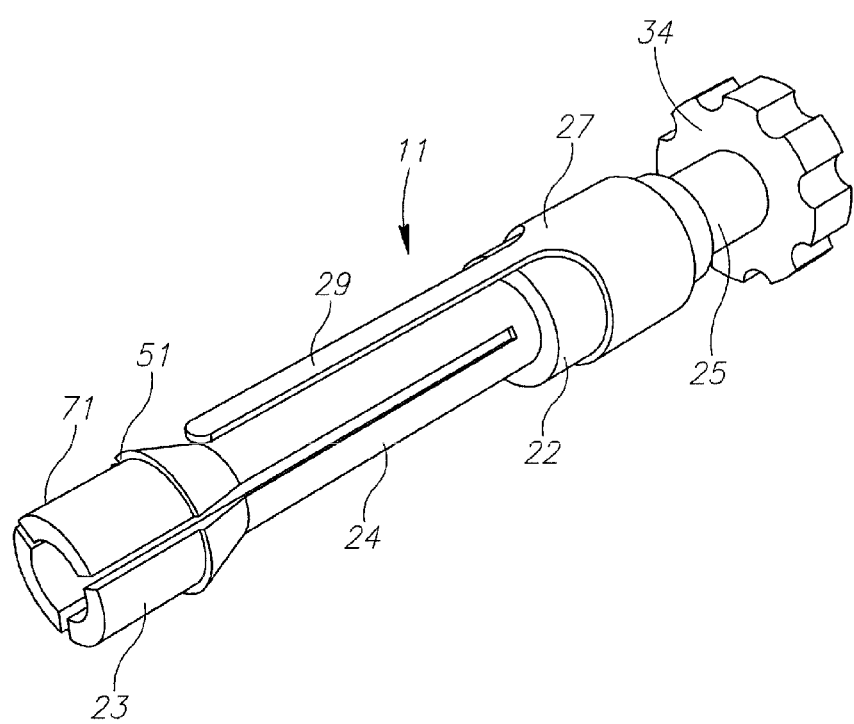
FIG. 1 is a schematic isometric illustration of an everting device according to one embodiment the present invention.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE PRESENT INVENTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

The device and method according to embodiments of the present invention may enable gradual everting of an edge of a tubular elastic graft over a fastener, for example in order to prepare the graft and the fastener for coupling, e.g., in an easy and or quick manner. This may be especially important, for example, when used in operating rooms. The device and method according to embodiments of the present invention may reduce, e.g., minimize stretching of the elastic graft, so that substantially no damage to the graft may be caused, and/or no substantially extreme requirements on the elasticity of the graft may be needed, e.g. even when the diameter of the graft decreases.

Reference is made to FIG. 1, which is a schematic illustration of an everting device 11 according to an embodiment of the invention. Everting device 11 may include everter 27, which may include a pliant tongue 29. Everter 27 may rotate around cylindrical member 22. Everter 27 may further slide axially on cylindrical member 22. Everting device 11 may also include a grip head 23. Grip head 23 may include an assembly having several segments 71 arranged around an axis of head 23. Segments 71 may be brought closer or pushed away from each other to modify an external diameter of grip head 23. The external diameter of grip head 23 may be modified when radial pressure is activated on grip head 23. For demonstration only, FIG. 1 shows three segments 71, but the number of segments 71 may vary. More segments 71 will provide more freedom in modifying the outer diameter of grip head 23, and may allow narrower slits between segments 71. Narrower slits may prevent obstructions to the movement of pliant tongue 29 when it rotates around grip head 23. Everting device 11 may also include a conical section 51. Conical section 51 may function, for example, as a limiter to axial movement of a fastener (not shown in FIG. 1), as described below. Conical section 51 may facilitate sliding of pliant tongue 29 under a tubular member (not shown in FIG. 1) laid on grip head 23 and extending over conical section 51, as described below. Everting device 11 may further include a flexibility section 24 which may provide flexibility to everting device 11 and may facilitate modifying of the external diameter of everting device 11 and grip head 23. The slits between segnients 71 may extend through conical section 51 and flexibility section 24, e.g., to allow further freedom in modifying the external diameter of grip head 23. Everting device 11 may also include a collet mandrel 25. Insertion of collet mandrel 25 into cylindrical member 22 may expand the diameter of flexibility section 24 and grip head 23 as described below. Insertion of collet mandrel 25 into cylindrical member 22 may be performed by, for example, mechanical force, hydraulic force, pneumatic force or a combination thereof. Collet mandrel 25 may include a knob 34 to facilitate rotation and thereby easy insertion and elicitation of collet mandrel 25 into cylindrical member 22, by, for example, a worm (not shown).

Figure 2:
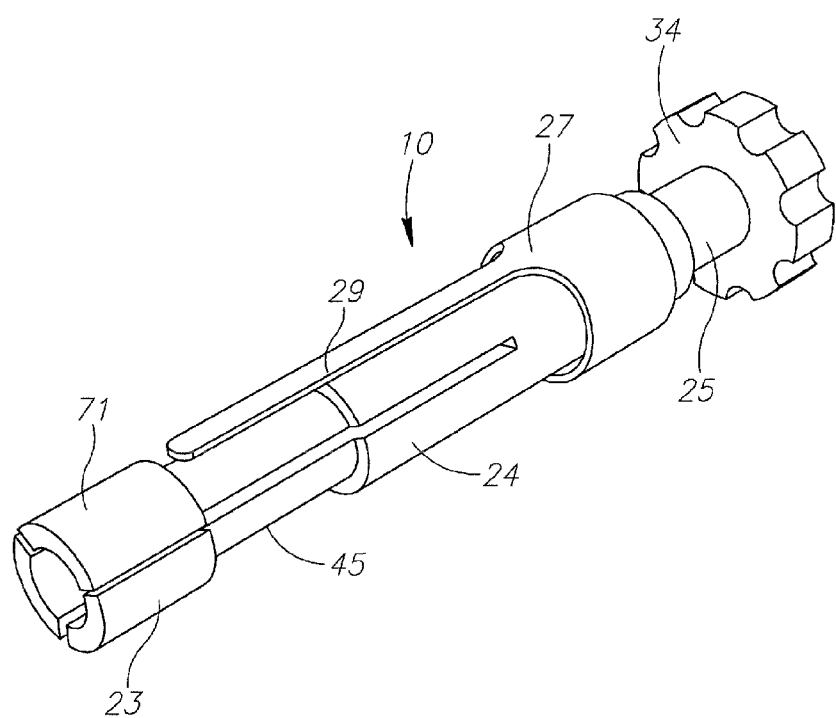
FIG. 2 is a schematic isometric illustration of an everting device according to another embodiment the present invention.

Reference is made to FIG. 2, which is a schematic illustration of an everting device 10 according to another embodiment of the invention. Although the invention is not limited in this respect, everting device 10 may have the same functionality as everting device 11 (shown in FIGS. 1, 8A-8E and 9A-9C). Everting device 10 may include a grooved section 45 between flexibility section 24 and grip bead 23, the slits extending through grooved section 45. Grooved section 45 may be used, for example, to hold means controlling the movement of pliant tongue 29, as described in detail below.

Figure 3:
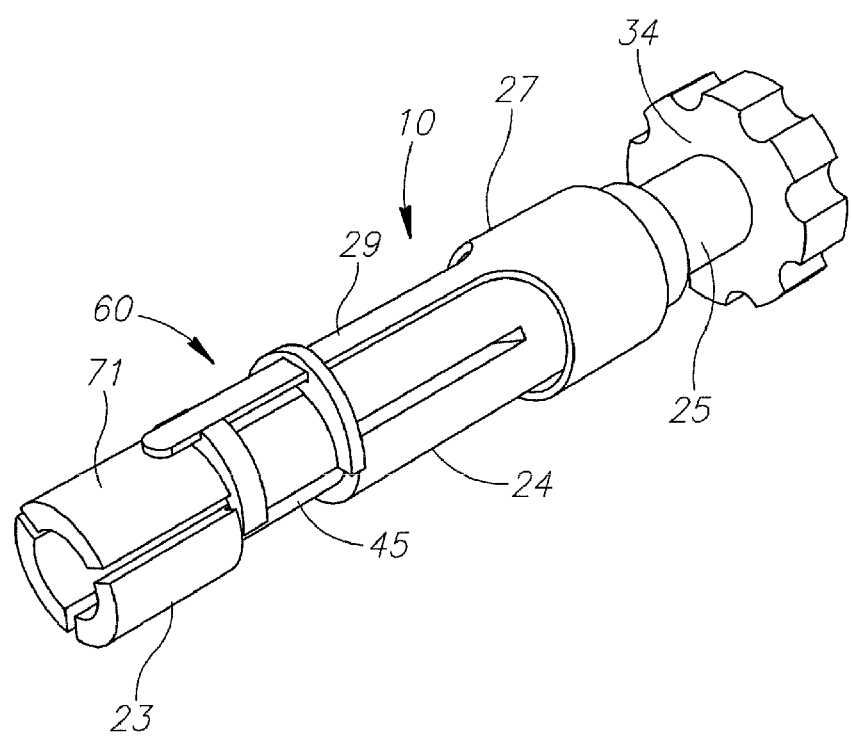
FIG. 3 is a schematic isometric illustration of an everting devite according to yet another embodiment the present invention.

Reference is made to FIG. 3, which is a schematic illustration of everting device 10 according to yet another embodiment of the invention. Springy cam 60 may be inserted on everting device 10. Springy cam 60 may limit lateral and/or radial movement of pliant tongue 29. Springy cam 60 may also position pliant tongue 29 in a desired radial position. Springy cam 60 may be rotatably supported on grooved section 45.

Figure 4:
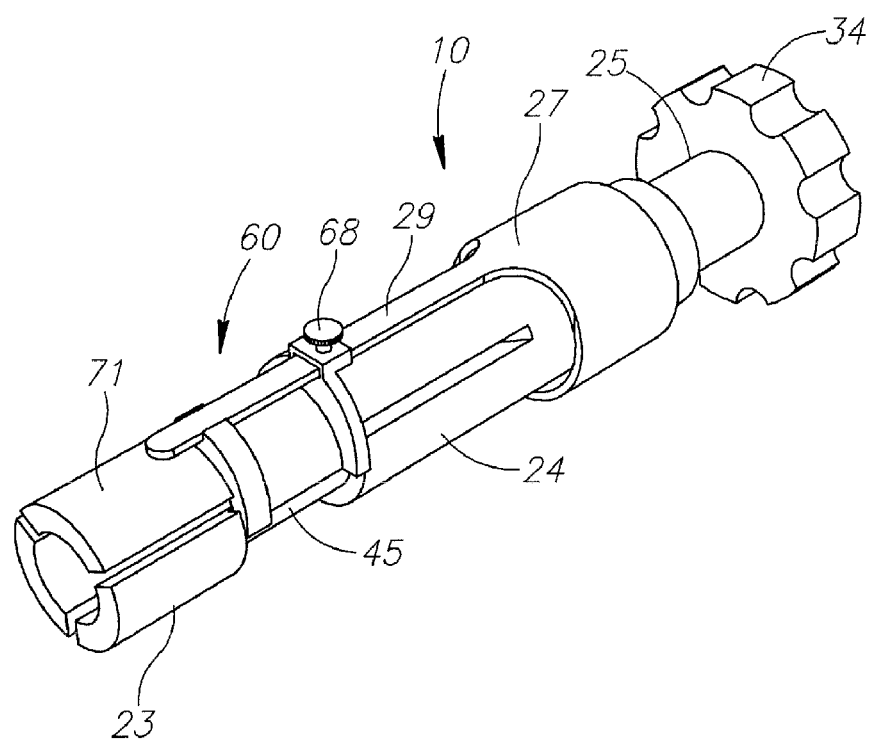
FIG. 4 is a schematic isometric illustration of an everting device according to yet another embodiment the present invention.

Reference is made to FIG. 4, which is a schematic illustration of everting device 10 according to yet another embodiment of the invention. Springy cam 60 may further include a regulator 68 to limit radial movement outwardly of pliant tongue 29, thus to control radial position of pliant tongue 29, to enable proper folding and everting of a tubular member as described below.

Figure 5:
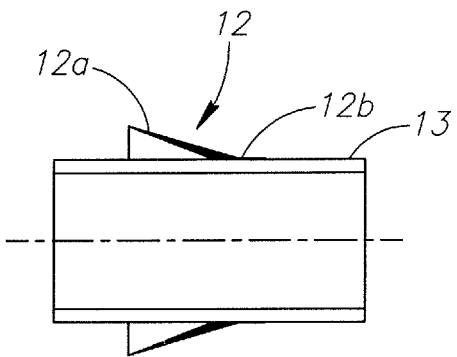
FIG. 5 is a schematic cross section illustration of fastener and graft which may be everted on the fastener.
Figure 9A:
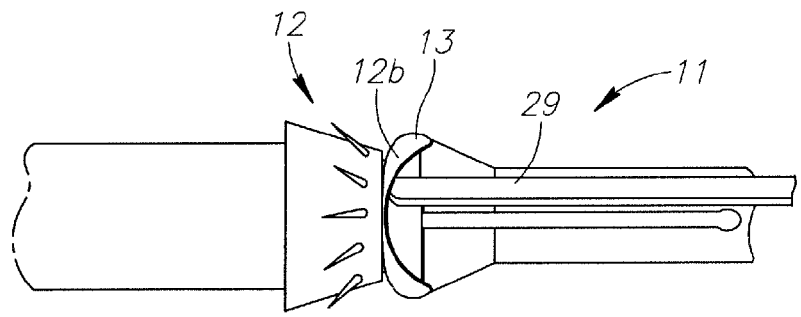
FIGS. 9A and 9B are partial schematic illustrations of an everting device according to one embodiment of the invention.
Figure 9B:
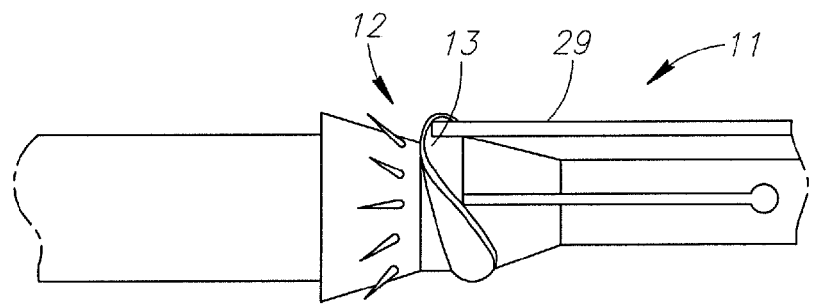

Reference is made to FIG. 5, which is a schematic cross section illustration of a fastener 12 and a graft 13 which may be everted on fastener 12 using the device and method according to embodiments of the present invention. Fastener 12 may have a conical portion 12$a$ and a cylindrical portion 12$b$. Inner diameters of cylindrical portion 12$b$ and of conical portion 12$a$ may coincide. Graft 13 may be inserted through conical portion 12$a$ and cylindrical portion 12$b$, :e.g. such that some portion of graft 13 may emerge out of cylindrical portion 12$b$, so as to be foldable over cylindrical portion 12$b$. Conical portion 12$a$ may be provided with a plurality of inclined barbs; as shown in FIGS. 9A and 9B. After fastener 12 and graft 13 are coupled using the device and method according to embodiments of the present invention, e.g., as described below, fastener 12 may be anchored to a blood vessel without sutures and/or in a quick manner. Fastener 12 may be formed of, for example, polymers, metals, special types of glass and other biocompatible materials. Graft 13 may be, for example, an artificial vascular graft or a natural graft made of a biological tissue.

Figure 6A:
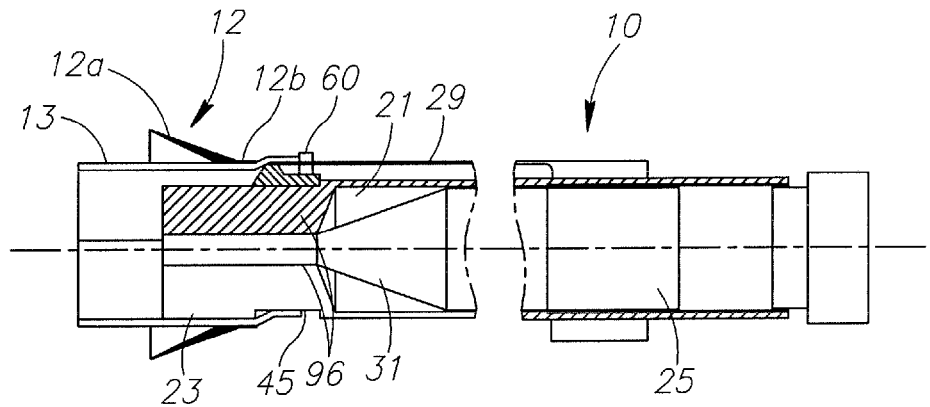
FIGS. 6A and 6B are partial schematic cross section illustrations of two conditions of a collet mandrel according to one embodiment of the invention.
Figure 6B:
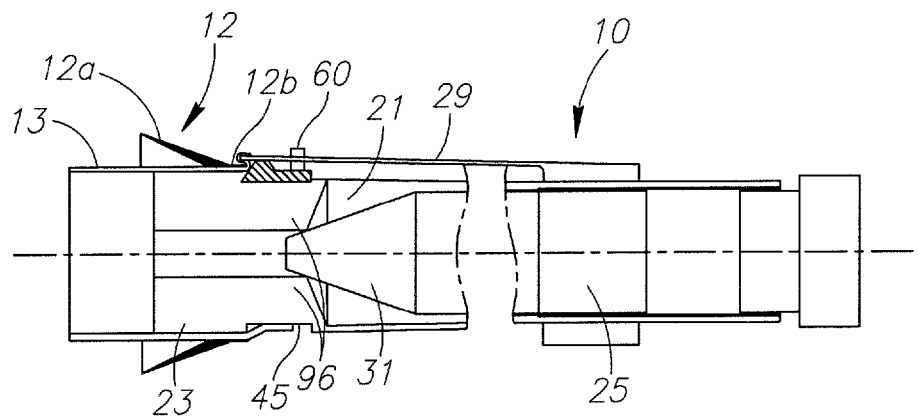

Reference is made to FIGS. 6A and 6B, which are partial schematic cross section illustrations of two conditions of collet mandrel 25 in everting device 10, according to one embodiment of the invention. Collet mandrel 25 may have a conical end 31. Collet mandrel 25 may be inserted into a cavity 21. When inserting collet mandrel 25 into cavity 21, conical end 31 may be pushed between internal supports 96 of segments 71 (FIG. 4), thus pushing internal supports 96 away from each other and expanding the external diameter of grip head 23. When the diameter of grip head 23 has expanded to reach firm gripping of fastener 12 and graft 13, insertion of collet mandrel 25 may be stopped and the axial movement of collet mandrel 25 may be locked, e.g. due to the mechanical arrangement of the worm of collet mandrel 25 or any other suitable locking arrangement (not shown). The portion of graft 13 that emerges out of cylindrical portion 12$b$ may then be stretched out, and pliant tongue 29 may be positioned in a required radial position to enable pliant tongue 29 to slide on cylindrical portion 12$b$, as seen in FIG. 6A. Springy cam 60 may be rotatably supported on grooved section 45 and may support pliant tongue 29, as described above. Pliant tongue 29 may slide axially towards fastener 12. A part of graft 13 which is in contact with pliant tongue 29 may he pushed up by pliant tongue 29 and may be folded over cylindrical portion 12$b$, as seen in FIG. 6B. Pliant tongue 29 may then be rotated to encircle cylindrical portion 12$b$. By rotation of pliant tongue 29, the portion of graft 13 that emerges out of cylindrical portion 12$b$ may be gradually everted over cylindrical portion 12$b$. When the eversion is completed, pliant tongue 29 may slide away from fastener 12. Collet mandrel 25 may then be pulled away from internal supports 96, e.g. by turning knob 34 backwards, thus enabling the external diameter of grip head 23 to be reduced. When the external diameter of grip head 23 is reduced, the gripping of fastener 12 and graft 13 on grip head 23 may be released, and fastener 12 together with graft 13 may be removed from grip head 23.

Figure 7:
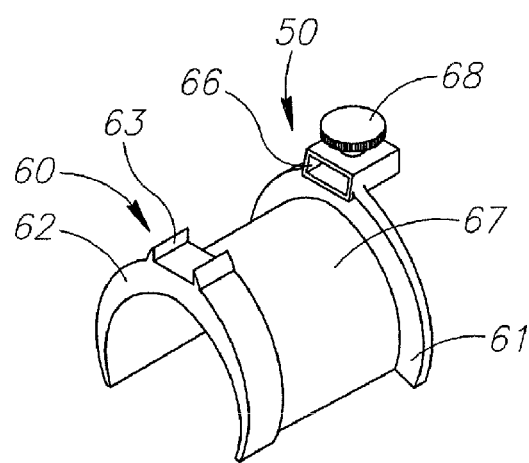
FIG. 7 is a detailed schematic isometric illustration of a springy cam according to one embodiment of the invention.

Reference is made to FIG. 7, which is a detailed schematic illustration of springy cam 50 according to one embodiment of the invention. Although the invention is not limited in this respect, springy cam 50 may have the same functionality as springy cam 60 (shown in FIGS. 3, 4, 6A-6B and 10A-10C). Springy cam 50 may include a first shoulder 62. First shoulder 62 may include a socket 63 to laterally support pliant tongue 29 (FIGS. 6A and 6B). First shoulder 62 may position pliant tongue 29 in a prescribed radial position. First shoulder 62 may provide barrier to limit insertion of fastener 12 (FIGS. 6A and 6B) onto grip head 23 (FIGS. 6A and 6B). According to some embodiments springy cam 50 may include a second shoulder 61. Second shoulder 61 may include a passage 64 to support pliant tongue 29 radially and/or axially. Passage 66 may further include a regulator 68 to limit radial position of pliant tongue 29 to enable proper folding and everting of an edge of graft 13 over cylindrical portion 12$b$. Second shoulder 61 may indicate proper length of the portion of graft 13 (FIGS. 6A and 6B) inserted onto grip head 23 (FIGS. 6A and 6B). The size of springy cam 50 may be chosen to match a diameter of a specific fastener 12. Springy cam 50 may include an arch 67. Arch 67 may be elastic. An internal diameter of arch 67 may be slightly smaller than an outer diameter of grooved section 45 (not shown). Springy cam 50 may be installed on grooved section 45 by pushing arch 67, e.g. forcefully, onto grooved section 45. A portion of the perimeter of grooved section 45 may be unoccupied by arch 67, thus preventing over stretching of graft 13.

Figure 8A:
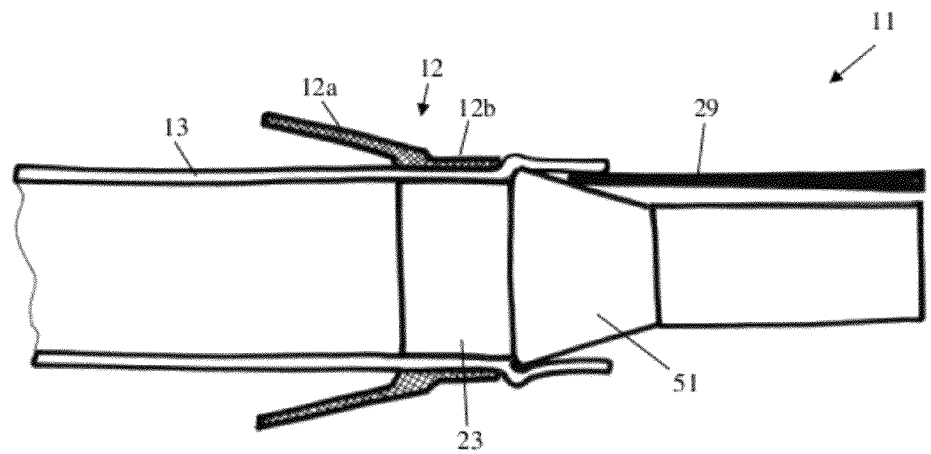
FIGS. 8A to 8E are partial schematic cross section illustrations of an everting device according to one embodiment of the invention.
Figure 8B:
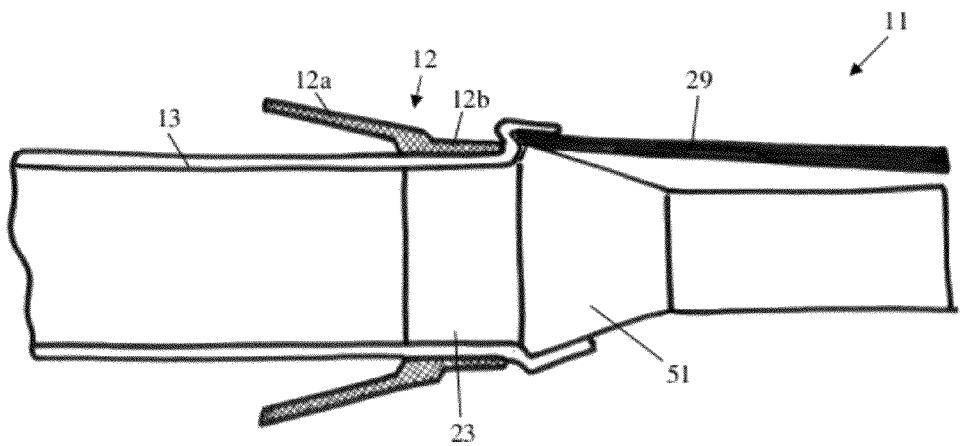
Figure 8C:
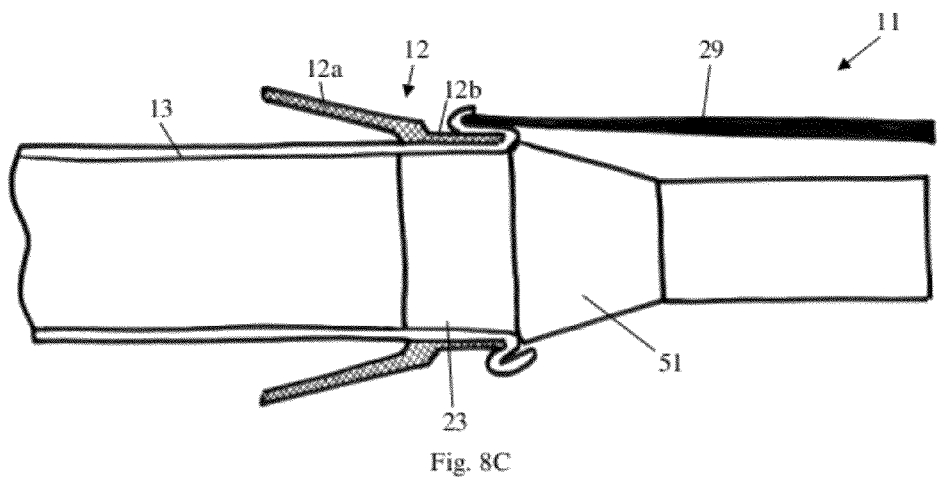
Figure 8D:
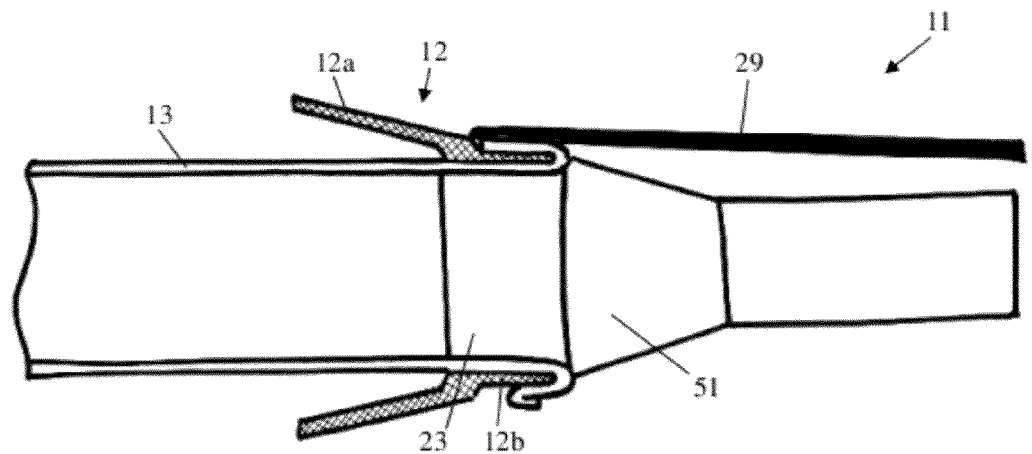
Figure 8E:
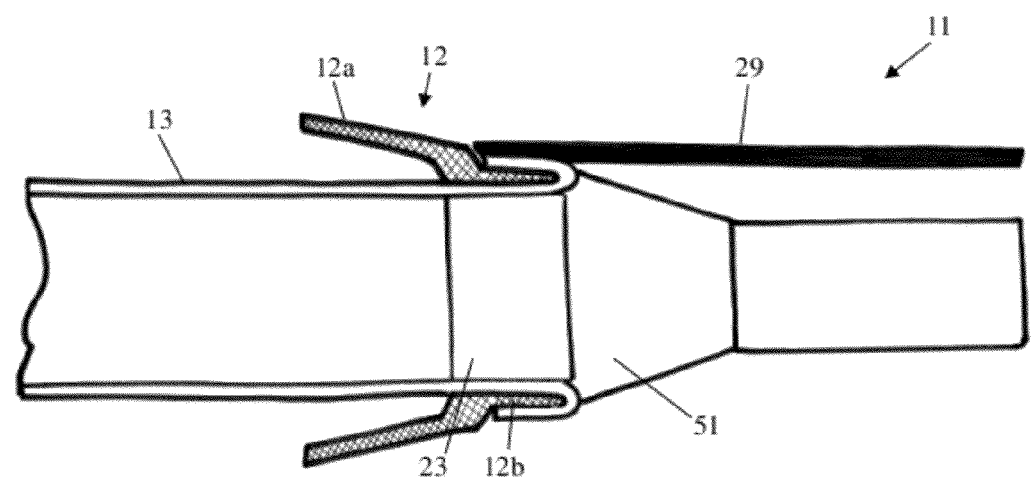

Reference is made to FIGS. 8A-8E, which are partial schematic cross section illustration of everting device 11 illustrating different stages of everting graft 13 onto fastener 12 according to an embodiment of the invention. FIGS. 9A and 9B are additional partial schematic illustrations of these stages. Graft 13 may be inserted on everting device 11 so that the end of graft 13 may rest upon a shoulder of conical section 51. Fastener 12 may be inserted on graft 13 until the outer edge of cylindrical portion 12$b$ meets the shoulder of conical section 51. In the embodiment illustrated in FIGS. 6A and 6B graft 13 may be inserted on everting device 11 until the end of graft 13 meets second shoulder 61 and fastener 12 may be inserted until the edge of cylindrical portion 12b meets first shoulder 62. The diameter of grip head 23 may then be adjusted to firmly hold fastener 12 and graft 13 together, for example by inserting collet mandrel 25 into cylindrical member 22, as described above with reference to FIGS. 6A and 6B. When inserting fastener 12 with graft 13 on device 11, pliant tongue 29 may slide on conical section 51 under the portion of graft 13 that emerges out of cylindrical portion 12b (FIG. 8A). The part of graft 13 that is in contact with pliant tongue 29 may be pushed up and inversely by pliant tongue 29 (FIG. 8B) and may be folded over the edge of fastener 12 by further sliding pliant tongue 29 axially over cylindrical portion 12b and turning pliant tongue 29 in a rotary motion (FIG. 8C). Pliant tongue 29 may then be further rotated to encircle cylindrical portion 12b. By rotation of pliant tongue 29, the portion of graft 13 that emerges out of cylindrical portion 12b may be gradually folded and everted over the edge of fastener 12 (FIGS. 8D and 8E). When pliant tongue 29 completes a substantially full circle around cylindrical portion 12b, the portion of graft 13 that emerges out of fastener 12 may be fully everted (FIG. 8E).

Figure 10A:
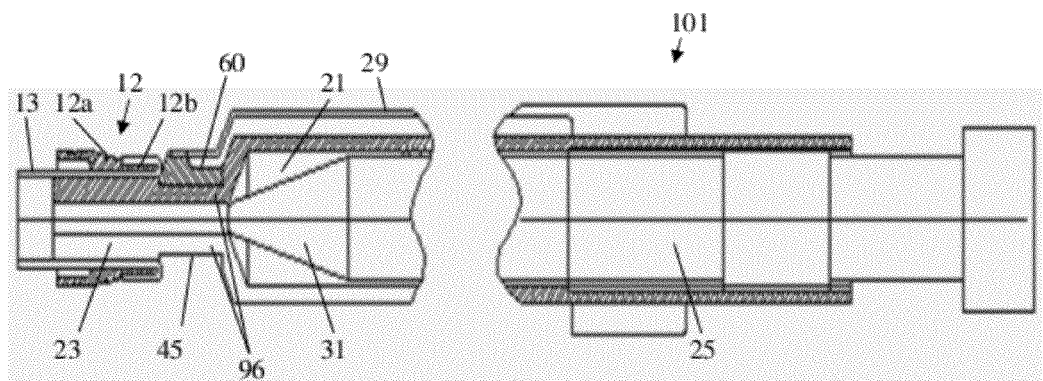
FIGS. 10A to 10C are partial schematic cross-sectional illustrations of everting devices according to embodiments of the invention.
Figure 10B:
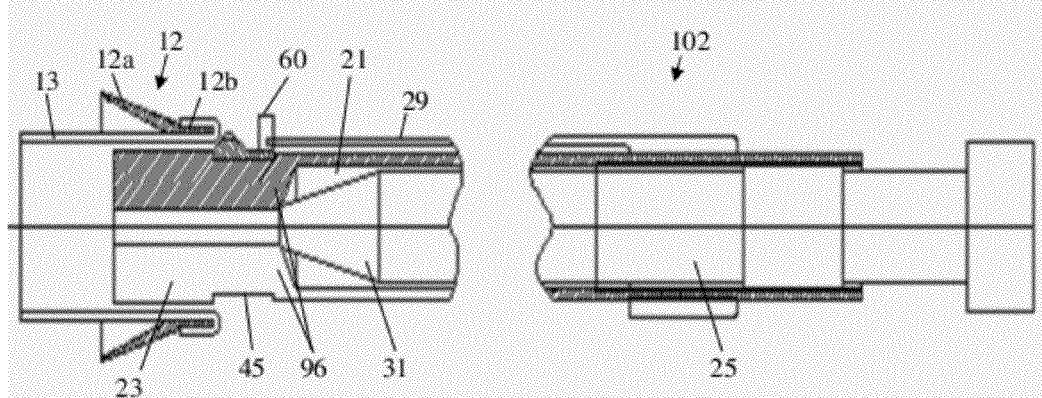
Figure 10C:
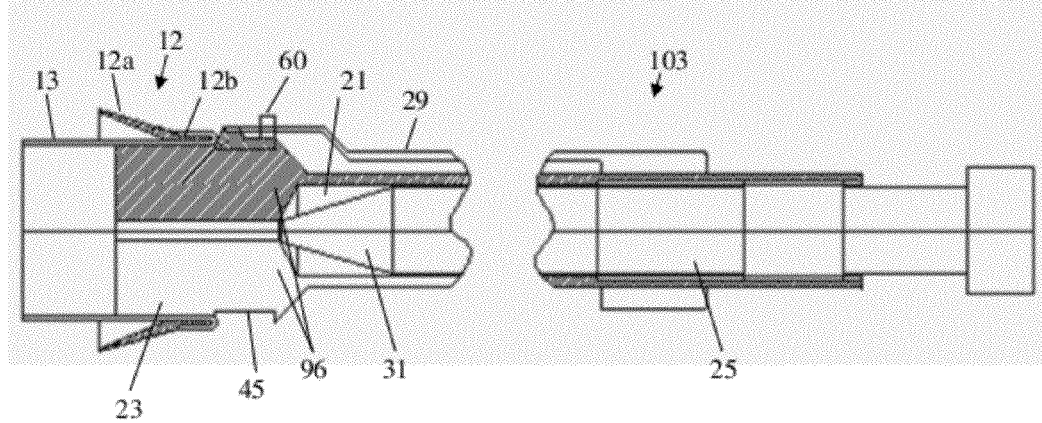

Reference is now made to FIGS. 10A to 10C, which are partial schematic cross-sectional illustrations of everting devices 101, 102, 103 according to some embodiments of the invention. Although the invention is not limited in this respect, everting devices 101, 102, 103 may have the same functionality as everting device 10 (shown in FIGS. 2-4 and 6A-6B) and/or everting device 11 (shown in FIGS. 1, 8A-8E and 9A-9C). Devices according to embodiments of the present invention may vary in shape and/or size to fit to, different diameters or diameter ranges of graft 13 and/or fastener 12. The shape and size of head 23 may vary in different embodiments of devices of the present invention to match different shapes and/or sizes of graft 13 and/or fastener 12. The shape and/or size of pliant tongue 29 may vary in different embodiments of devices of the present invention to match different shapes and/or sizes of graft 13 and/or fastener 12. FIGS. 10A to 10C show, for example, different shapes and different relative sizes of head 23, pliant tongue 29, collet mandrel 25, conical end 31 and springy cam 60, so as to fit different diameters and/or ranges of diameters of graft 13 and/or fastener 12, e.g. while maintaining the functionalities of gripping of fastener 12 with graft 13, everting of the end of graft 13 and releasing fastener 12 with everted graft 13 substantially, as described above.

Figure 11:
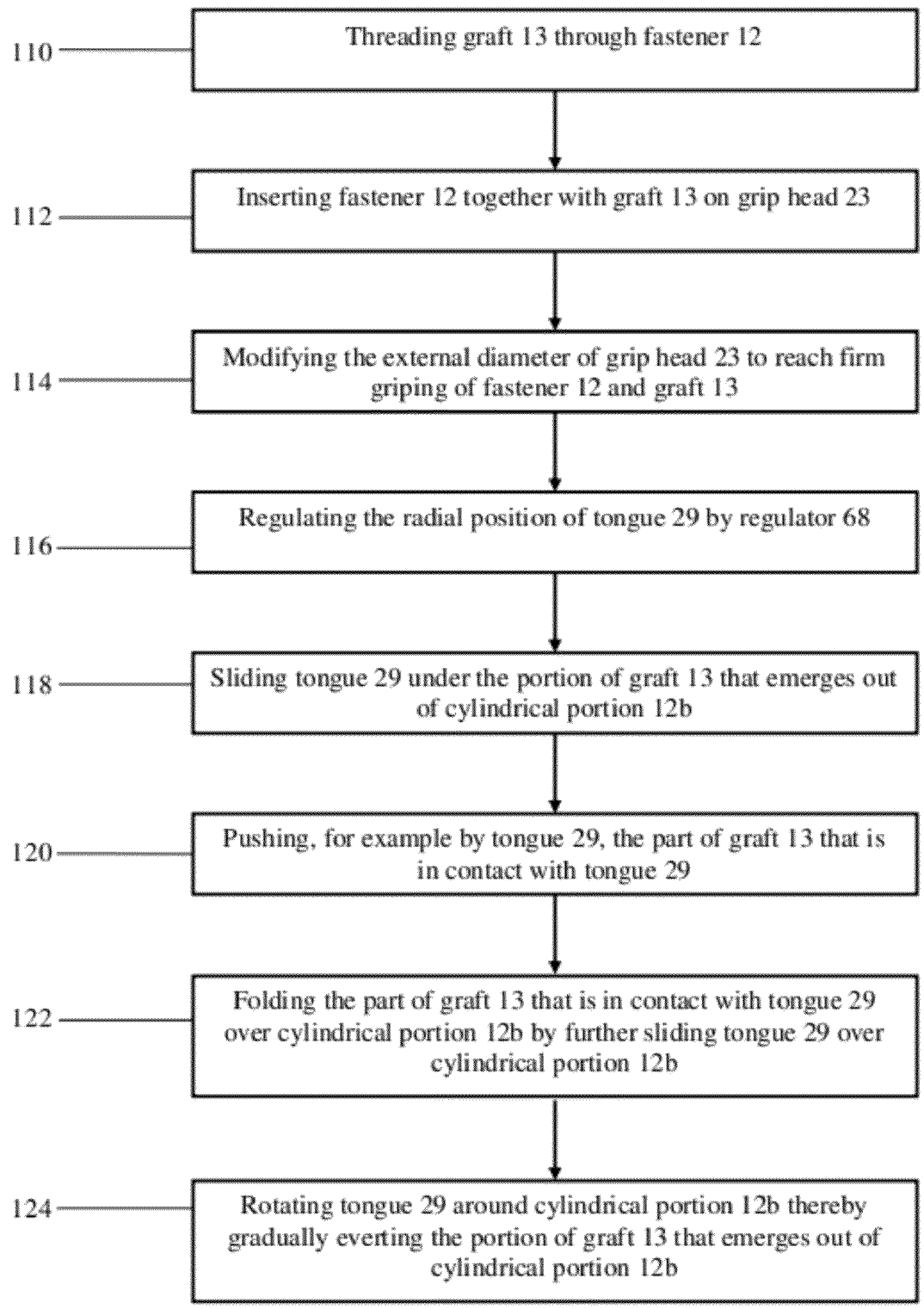
FIG. 11 is a flowchart describing a method according to one embodiment of the invention.

Reference is made to FIG. 11, which is a flowchart describing a method for everting an edge of graft 13 over the edge of fastener 12 according to one embodiment of the invention. As indicated in block 110, the method may include threading graft 13 through fastener 12. As indicated in block 112, the method may include, inserting graft 13 and fastener 12 on grip head 23. As indicated in block 114, the method may include modifying the external diameter of grip head 23 thereby reaching firm griping of fastener 12 and graft 13. As indicated in block 116, the method may include regulating the radial position of pliant tongue 29, for example by regulator 68. As indicated in block 118, the method may include sliding pliant tongue 29 under the portion of graft 13 that emerges out of cylindrical portion 12b. As indicated in block 120, the method may include pushing, for example by pliant tongue 29, the part of graft 13 that is in contact with pliant tongue 29. As indicated in block 122, the method may include The method of FIG. 11 may further include folding the part of graft 13 that is in contact with pliant tongue 29 over cylindrical portion 12b, for example by further sliding pliant tongue 29 over cylindrical portion 12b. As indicated in block 124, the method may include rotating pliant tongue 29 around cylindrical portion 12b thereby gradually everting the portion of graft 13 that emerges out of cylindrical portion 12b.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

What is claimed is:

1. An everting device for everting an edge of a tubular elastic graft over a fastener, the device comprising:
    a tubular body comprising a grip head at a distal end wherein an external diameter of said head is modifiable, said grip head is to grip a tubular elastic object inserted through a tubular inelastic object and inserted on said grip head, wherein an edge of said elastic object is emergable out of said inelastic object; and
    a pliant tongue rotatable around said tubular body, wherein radial position of said tongue with respect to the axis of said tubular body is adjustable, wherein said tongue is axially slidable towards said grip head or away from said grip head, said pliant tongue is to:
        fold a part of said edge of elastic object being in contact with said tongue over an edge of said inelastic object by sliding said tongue over said inelastic object; and
        evert said edge of elastic object over said inelastic object by rotating said tongue around said inelastic object and sliding said pliant tongue axially toward said grip head.

2. A device according to claim 1, wherein said grip head comprises at least three segments, said segments can be brought closer or pushed away from each other to modify the external diameter of said grip head.

3. A device according to claim 2, further comprising a collet mandrel insertable into said tubular body to push away said segments thus to enlarge the external diameter of said grip head.

4. A device according to claim 1, further comprising a springy cam rotatable around said tubular body to limit at least one of lateral movement and radial movement of said tongue.

5. A device according to claim 4, wherein said springy cam is adapted to firmly position said tongue in a prescribed radial position.

6. A device according to claim 4, wherein said springy cam comprises a first shoulder to limit insertion of said inelastic object on said grip head.

7. A device according to claim 6, wherein said springy cam comprises a second shoulder to indicate proper insertion of said elastic object.

8. A device according to claim 4, wherein said springy cam further comprising a regulator to control radial position of said tongue.

9. A device according to claim 1, wherein said tubular body comprises a conical section, wherein said tongue is slidable on said conical section.

10. A device according to claim 9, wherein said conical section includes a shoulder to limit insertion of said inelastic object on said grip head.

11. A device according to claim 1, wherein said elastic object is a vessel graft.

12. A device according to claim 11, wherein said inelastic object is a fastener adapted to couple said graft to a vessel.

13. A method for everting an edge of a tubular elastic graft over a fastener, the method comprising:
- threading a tubular elastic object through a tubular inelastic object until an edge of said elastic object emerges out of said inelastic object substantially longer than the length of said inelastic object;
- gripping said inelastic object together with said threaded elastic object by a grip head at a first end of an everting device, the everting device comprising:
  - a tubular body comprising a grip head at a distal end wherein an external diameter of said head is modifiable; and
  - a pliant tongue rotatable around said tubular body, wherein radial position of said tongue with respect to the axis of said tubular body is adjustable, wherein said tongue is axially slidable towards said grip head or away from said grip head;
- inserting said tubular inelastic object together with said tubular elastic object onto said grip head until an edge of said tubular inelastic object reaches a shoulder of said tubular body;
- pushing by said pliant tongue a part of said edge of elastic object being in contact with said tongue;
- folding said part of said edge of elastic object over an edge of said inelastic object by sliding said tongue over said inelastic object;
- everting said edge of elastic object over said inelastic object by rotating said tongue around said inelastic object and sliding said pliant tongue axially toward said grip head.

14. A method according to claim 13, wherein said gripping comprising inserting said inelastic object together with said threaded elastic object onto a grip head and modifying the external diameter of said grip head to reach firm griping of said inelastic object and said threaded elastic object.

15. A method according to claim 13, further comprising, before pushing, sliding said tongue under said edge of said elastic object.

16. A method according to claim 13, further comprising regulating the radial position of said tongue.

17. A method according to claim 13, further comprising at least one of sliding said pliant tongue away from said inelastic object, reducing external diameter of said grip head and removing said elastic object and said inelastic object from said grip head.

* * * * *